United States Patent
Babaev (10) Patent No.: US 7,842,032 B2
(45) Date of Patent: *Nov. 30, 2010

(54) APPARATUS AND METHODS FOR THE SELECTIVE REMOVAL OF TISSUE

(75) Inventor: Eilaz Babaev, Minnetonka, MN (US)

(73) Assignee: Bacoustics, LLC, Minnetonka, MN (US)

(*) Notice: Subject to any disclaimer, the term of this patent is extended or adjusted under 35 U.S.C. 154(b) by 895 days.

This patent is subject to a terminal disclaimer.

(21) Appl. No.: 11/737,112

(22) Filed: Apr. 18, 2007

(65) Prior Publication Data

US 2007/0233054 A1 Oct. 4, 2007

Related U.S. Application Data

(63) Continuation-in-part of application No. 11/250,870, filed on Oct. 13, 2005, now Pat. No. 7,572,268.

(51) Int. Cl.
*A61B 18/18* (2006.01)

(52) U.S. Cl. ......................... 606/20; 606/169
(58) Field of Classification Search ................... 606/20, 606/169–170
See application file for complete search history.

(56) References Cited

U.S. PATENT DOCUMENTS

| | | | |
|---|---|---|---|
| 3,220,414 A | 11/1965 | Johnston |
| 3,237,623 A | 3/1966 | Gordon |
| 3,589,363 A | 6/1971 | Banko et al. |
| 3,889,680 A | 6/1975 | Amao |
| 4,015,606 A | 4/1977 | Mitchiner et al. |
| 4,082,096 A | 4/1978 | Benson |
| 4,528,979 A | 7/1985 | Marchenko et al. |
| 4,823,790 A | 4/1989 | Alperovich et al. |
| 4,832,022 A | 5/1989 | Tjulkov et al. |
| 4,946,460 A | 8/1990 | Merry et al. |
| 5,078,713 A | 1/1992 | Varney |
| 5,108,390 A | 4/1992 | Potocky |
| 5,139,496 A | 8/1992 | Hed |
| 5,334,181 A | 8/1994 | Rubinsky et al. |
| 5,433,717 A | 7/1995 | Rubinsky et al. |
| 5,452,582 A | 9/1995 | Longsworth |
| 5,520,682 A | 5/1996 | Baust et al. |
| 5,649,936 A | 7/1997 | Real |
| 5,716,353 A | 2/1998 | Matsuura et al. |
| 5,899,898 A | 5/1999 | Arless et al. |
| 5,899,899 A | 5/1999 | Arless |
| 5,906,612 A | 5/1999 | Chinn |

(Continued)

FOREIGN PATENT DOCUMENTS

WO WO 01/76517 10/2001

OTHER PUBLICATIONS

Mark D. Andrews, Cryosurgery for Common Skin Conditions, American Family Physician, vol. 69 (10), May 15, 2005, pp. 2365-2372.

*Primary Examiner*—Todd E Manahan
*Assistant Examiner*—Diane Yabut (57) ABSTRACT

An Ultrasonic apparatus and method is provided for the selective and targeted removal of unwanted tissues. The apparatus and methods may utilize combinations of ultrasonic and cryogenic energy for the selective removal tissue. The apparatus generates and delivers to the tissue cryogenic and ultrasonic energy, either in combination or in sequence, provides resize ablation of unwanted tissue parts, and may be used on various body tissues including internal organs.

16 Claims, 8 Drawing Sheets

U.S. PATENT DOCUMENTS

| | | | |
|---|---|---|---|
| 5,913,885 A | 6/1999 | Klatz et al. | |
| 5,916,242 A | 6/1999 | Schwartz | |
| 5,957,963 A | 9/1999 | Dobak, III | |
| 6,030,412 A | 2/2000 | Klatz et al. | |
| 6,039,730 A | 3/2000 | Rabin et al. | |
| 6,041,787 A | 3/2000 | Rubinsky | |
| 6,042,579 A | 3/2000 | Elsberry et al. | |
| 6,045,532 A | 4/2000 | Eggers et al. | |
| 6,051,019 A | 4/2000 | Dobak, III et al. | |
| 6,074,412 A | 6/2000 | Mikus | |
| 6,083,166 A | 7/2000 | Holdaway et al. | |
| 6,096,068 A | 8/2000 | Dobak, III et al. | |
| 6,106,518 A | 8/2000 | Wittenberger et al. | |
| 6,126,684 A | 10/2000 | Gobin et al. | |
| 6,149,677 A | 11/2000 | Dobak, III et al. | |
| 6,245,095 B1 | 6/2001 | Dobak, III et al. | |
| 6,248,126 B1 | 6/2001 | Lesser et al. | |
| 6,280,439 B1 * | 8/2001 | Martin et al. | 606/21 |
| 6,280,441 B1 | 8/2001 | Ryan | |
| 6,386,202 B1 | 5/2002 | Frazee | |
| 6,413,263 B1 | 7/2002 | Lobdill et al. | |
| 6,475,212 B2 | 11/2002 | Dobak et al. | |
| 6,546,932 B1 | 4/2003 | Nahon et al. | |
| 6,551,309 B1 | 4/2003 | Lepivert | |
| 6,565,556 B1 | 5/2003 | Korpan et al. | |
| 6,582,368 B2 | 6/2003 | Holdaway et al. | |
| 6,648,880 B2 | 11/2003 | Chauvet et al. | |
| 6,663,554 B2 | 12/2003 | Babaev | |
| 6,786,902 B1 | 9/2004 | Rabin et al. | |
| 6,858,025 B2 | 2/2005 | Maurice | |
| 6,936,045 B2 | 8/2005 | Yu et al. | |

* cited by examiner

APPARATUS AND METHODS FOR THE SELECTIVE REMOVAL OF TISSUE

CROSS REFERENCE TO RELATED APPLICATIONS

This application is a continuation-in-part of U.S. patent application Ser. No. 11/250,870, filed Oct. 13, 2005, now U.S Pat. No. 7,572,268, the teachings of which are hereby incorporated by reference.

BACKGROUND OF THE INVENTION

1. Field of the Invention

The present invention relates to the removal of tissue from a patient, and more particularly, to apparatuses and methods using combinations of ultrasonic and cryogenic energy to remove tissue.

2. Description of the Related Art

Generally defined as diseases affecting the skin, skin disorders are common ailments afflicting individuals. Skin disorders frequently affect multiple layers of the skin. Some common skin disorders include wrinkles, scars, warts, non-metastsis melanomas, basilomas, human papillomaviruses, and various pre-cancerous or cancerous skin growths. Typical methods for treating skin disorders include surgical removal, chemical peeling, cryogenic destruction of diseased tissue, and various electrical treatments.

SUMMARY OF THE INVENTION

The present invention is directed towards apparatuses and methods for the selective ablation of unwanted tissue. Delivering ultrasonic and cryogenic energies simultaneously and/or sequentially, the present invention may destroy and/or remove unwanted tissue. The present may also be used to remove diseased tissue. External skin tissue and/or internal tissues of the body may be treated with the present invention. The present invention may be utilized for the selective removal of targeted tissue hard and/or soft tissue.

Combining the delivery of ultrasonic and cryogenic energy during treatment, the present invention may provide advantages over existing methods and devices for removing unwanted and/or diseased tissue. One advantage may be avoiding the adhesion of cold elements to the tissue during cryogenic ablation. Another advantage may be that the vibration created by the ultrasonic energy delivered to the tissue separates the unwanted and/or diseased tissue from healthy and/or wanted tissue. Another advantage may the destruction of microorganisms in the treatments by the delivered ultrasonic and/or cryogenic energy. Another advantage may be the creation of an analgesic effect on the treated tissue by the delivered ultrasonic energy. Delivering ultrasonic energy before, during, and/or after ablation may increase healing time and/or provide other positive benefits to the surviving tissue.

An apparatus in accordance with the present invention may be embodied as a hand held device having a proximate end and a distal end. The proximate end may comprise a handle. The distal end may comprise an ultrasonic tip. The ultrasonic may comprise a body. The body may define one or more chambers. Delivering a cryogenic fluid, such as, but not limited to, a liquid or gas, into one or more of the chambers may cool the ultrasonic tip. Transferring thermal energy away from the tissue, the ultrasonic tip when sufficiently cooled and placed proximate to the tissue may ablate unwanted and/or diseased by freezing the tissue.

Causing the tip to vibrate at an ultrasonic frequency, an ultrasonic transducer mechanically connected to the ultrasonic tip may be used to excite the ultrasonic tip. The ultrasonic tip may be simultaneously excited and cooled. Alternatively, the ultrasonic tip may be sequentially cooled and excited. Simultaneously transferring thermal energy away from the tissue and transmitting ultrasonic energy to the tissue, the cooled and excited ultrasonic tip, when placed proximate to a tissue, may selectively ablate the targeted tissue. Sequentially transferring thermal energy away from the tissue and transmitting ultrasonic energy to the tissue, the sequentially cooled and excited ultrasonic tip, when placed proximate to a tissue, may, in the alternative, selectively ablate the target tissue. Targeting selected tissue, the present invention removes diseased and/or unwanted tissue without unduly damaging healthy tissues surround the targeted tissue.

The cryogenic fluid may be delivered to the chambers of the ultrasonic tip's body through one or more connecting tubes or similar elements. Acting as inlets, the connecting tubes introduce cryogenic fluid from a reservoir into a chamber. Acting as outlets, the connecting tubes permit cryogenic fluid to flow through and/or out of a chamber. A chamber may be designed to approach the distal end of the ultrasonic tip.

Exciting the distal end of the ultrasonic tip may enable the transmission of ultrasonic energy to a tissue. The transmission of ultrasonic energy to a tissue may occur during, before, and/or after the transfer of thermal energy away from the tissue. The transmission of ultrasonic energy and/or the transfer of thermal energy may occur through direct contact of the ultrasonic tip with the tissue. Alternatively, an accumulation of frost on the tissue and/or the ultrasonic tip may act as a conduit for the transfer of thermal energy and/or transmission of ultrasonic energy. A spray of cryogenic fluid emanating from an orifice in the ultrasonic tip may also be used as a conduit for the transfer of thermal energy and/or transmission of ultrasonic energy.

DETAILED DESCRIPTION OF THE INVENTION

The present invention is directed towards apparatuses and methods for the selective ablation of unwanted and/or diseased tissue by delivering ultrasonic and cryogenic energies simultaneously and/or sequentially to the tissue to be ablated. Embodiments of the present invention may result in a highly controllable and precise ablation of tissue.

Figure 1:
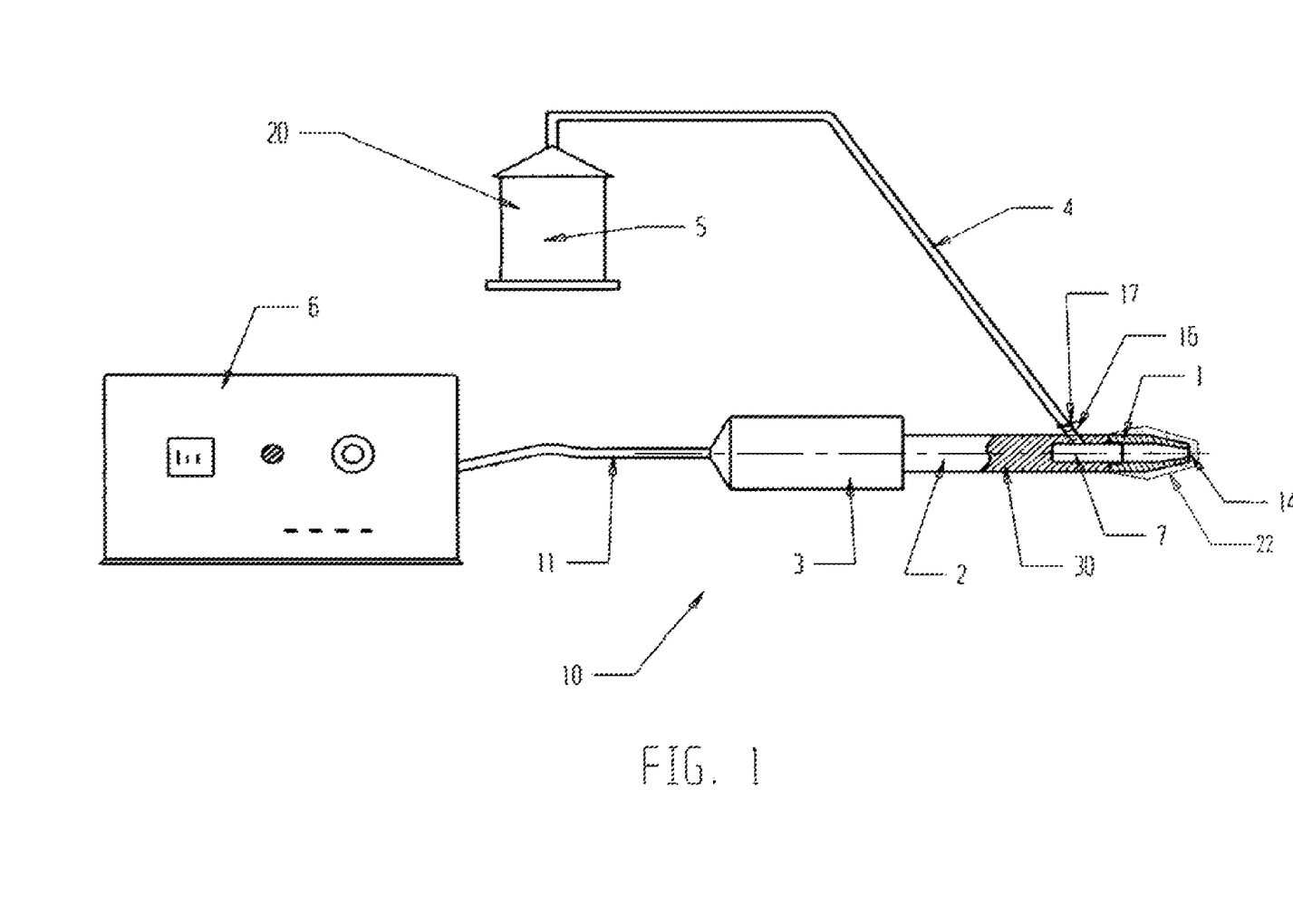
FIG. 1 is a general diagrammatic overview of an embodiment of a system for the removal of tissue with a combination of ultrasonic and cryogenic energy.

A general view of an embodiment of one apparatus 10 in accordance with the present invention is depicted in FIG. 1. The apparatus of the present invention 10 may be a hand held device with a distal ultrasonic tip 1. Ultrasonic tip 1 may be used to deliver cryogenic and ultrasonic energy to the tissue area 9. Ultrasonic tip 1 comprises a body defining one or more interior chambers 7 into which cryogenic fluid 20 flows. Cryogenic fluid 20 may be a liquid and/or gas. One example of possible cryogenic fluid is liquid nitrogen. Other suitable cryogenic fluids are readily recognizable by people of ordinary skill in the art. Cryogenic fluid 20 may be delivered to the interior chambers 7 from a source 5 through delivery tube 4. Delivery tube 4 is attached to the ultrasonic tip 1 at the inlet tube 16. Defining an interior passage 17, inlet tube 16 connects delivery tube 4 to chambers 7. Ultrasonic transducer 3 may be connected to an ultrasound generator 6 by a cable 11. Ultrasonic tip 1 provides an ultrasonically active distal end 14 and/or cryogenic energy to tissue 9 through direct contact or through accumulation of frost 22.

Creating accumulation of frost 22 on distal end 14 of the ultrasonic tip 1 may be accomplished by allowing moisture from the air to condense and freeze on distal end 14. Alternatively, a substance such as, but not limited, water may be placed on distal end 14 and allowed to freeze.

Ultrasonic tip 1 is usually made from a metal such as titanium. Ultrasonic tip 1 may also be made from plastic and disposed of after treatment. Ultrasonic tip 1 may be excited by ultrasonic transducer 3. Ultrasonic tip 1 may be connected to ultrasonic transducer 3 through an ultrasonic horn 2. Ultrasonic tip 1 may be a separate piece attachable to ultrasonic horn 2. Alternatively, ultrasonic tip 1 and ultrasonic horn 2 may form a single piece. Ultrasonic transducer 3 typically receives power from generator 6 through cable 11. Ultrasonic transducer 3 may be pulsed according to a drive signal generated by generator 6 and transmitted to ultrasonic transducer 3 by cable 11. The drive signal may be rectangular, trapezoidal, sinusoidal, or other signal types readily recognizable by those skilled in the art. Ultrasonic transducer 3 may be made to operate a frequency of approximately 18 KHz to approximately 20 MHz. The preferred frequency of operation is approximately 20 KHz to approximately 60 KHz. The recommended frequency of operation is approximately 35 KHz. The amplitude of the ultrasonic waves generated by transducer 3 may be approximately 1 micron to approximately 200 microns. The preferred amplitude of the ultrasonic waves generated by transducer 3 is approximately 50 microns.

Figure 2:
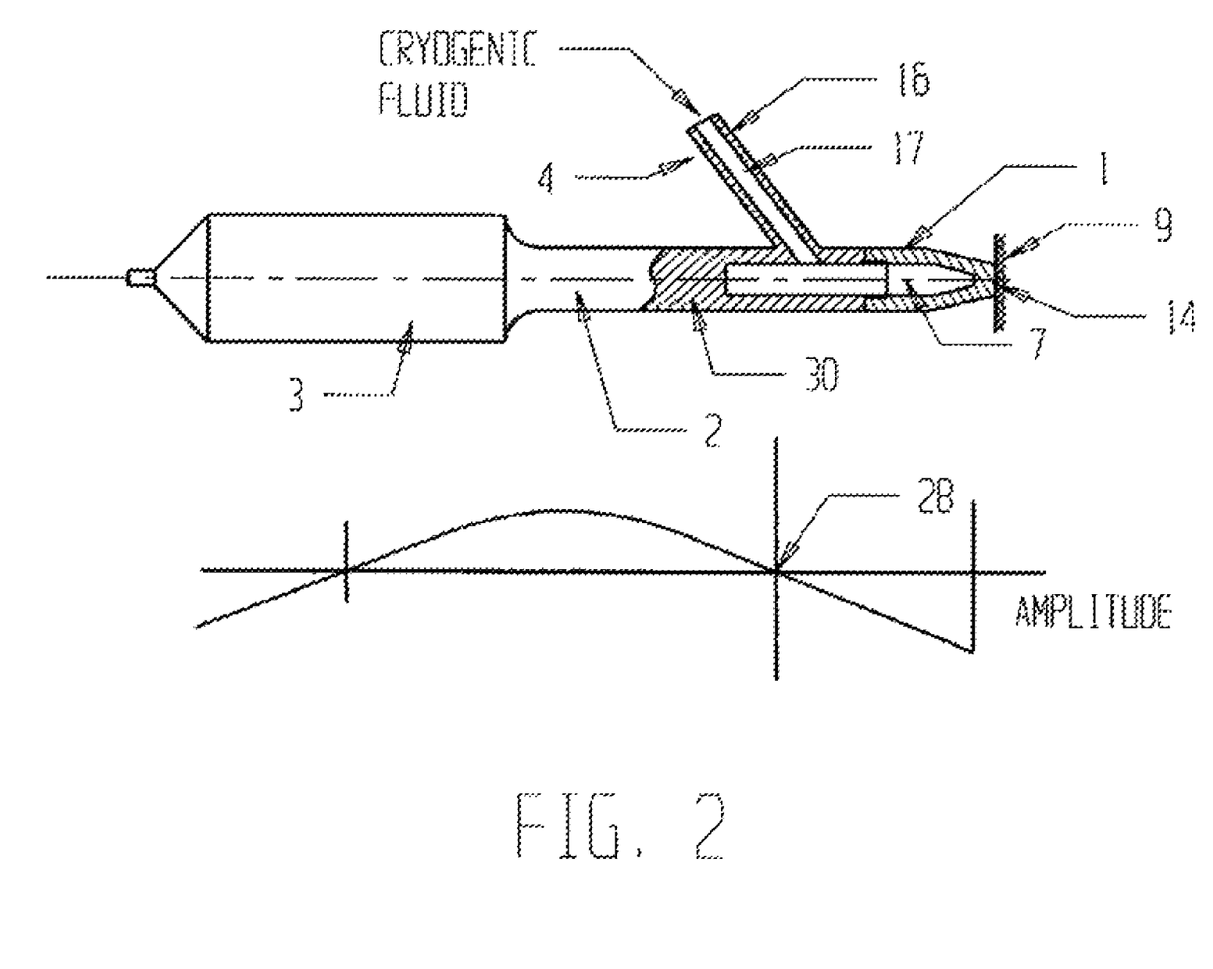
FIG. 2 shows an apparatus in accordance with present invention and a plot of the amplitude of the mechanical vibration of the ultrasonic horn and ultrasonic tip elicited by the transducer.

FIG. 2 shows an apparatus in accordance with present invention and a plot of the amplitude of the mechanical vibration of ultrasonic horn 2 and ultrasonic tip 1 elicited by transducer 3. Delivery tube 16 defines interior passage 17, which opens into chamber 7. Delivery tube 16 is attached to ultrasonic horn 2 approximately at the mechanical resonance node 28. A resonance is node is a point where the vibration amplitude of ultrasonic horn 2 or tip 1 is zero.

Figure 3:
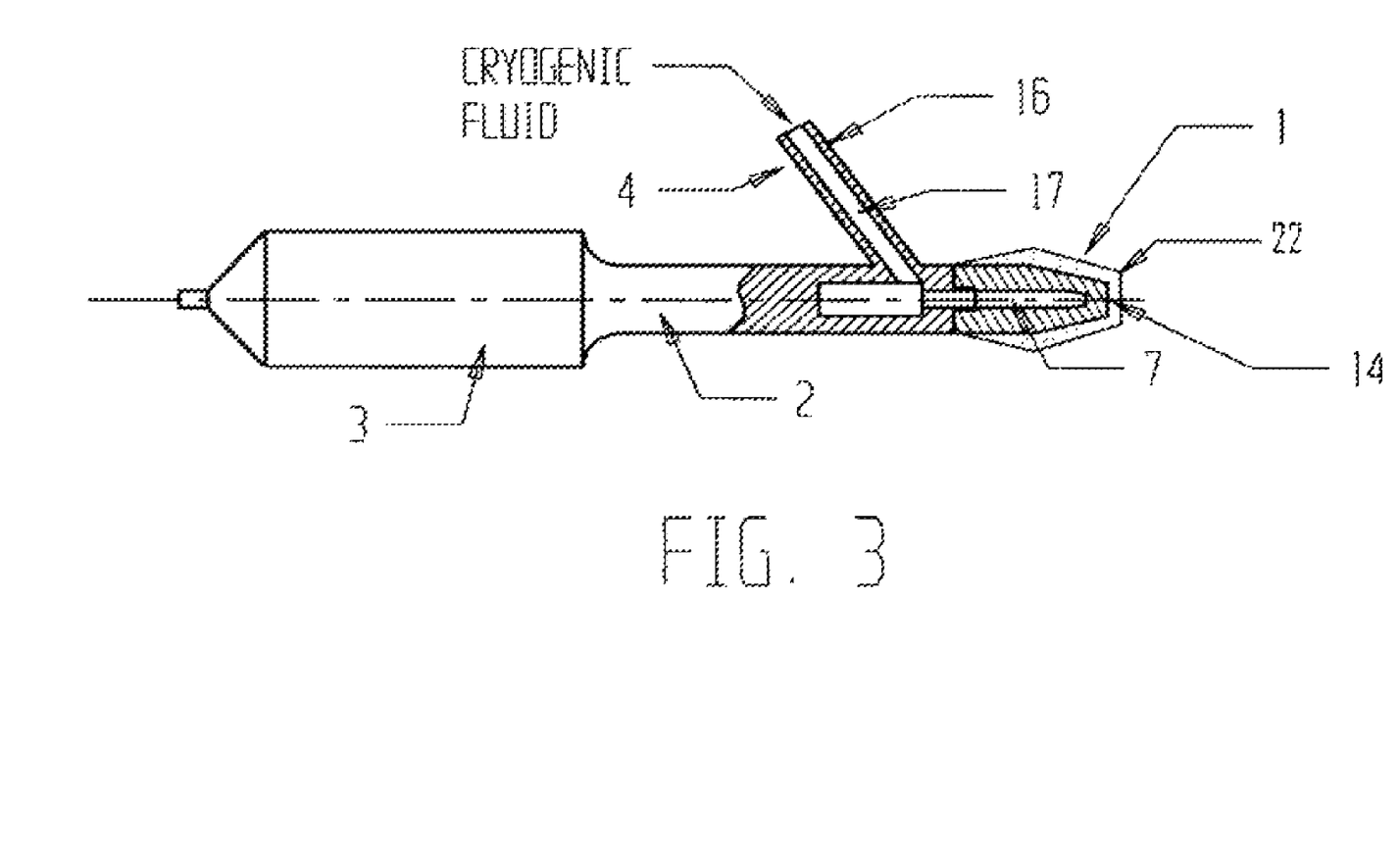
FIG. 3 shows an alternative embodiment of an apparatus in accordance with the present invention comprising a narrow elongated a chamber extending towards the distal end the ultrasonic tip.

FIG. 3 shows an alternative embodiment of an apparatus in accordance with the present invention. Ultrasonic tip 1, in the depicted embodiment, comprises a narrow elongated chamber 7 extending towards distal end 14.

Providing more than one chamber 7 may increase the efficacy of cryogenic ablation.

Figure 10:
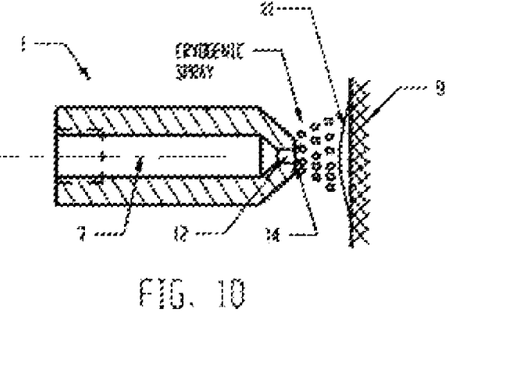
FIG. 10 illustrates an embodiment of the delivery of ultrasonic energy to the tissue through a cryogenic spray emitted toward the tissue from the radiation surface.
Figure 11:
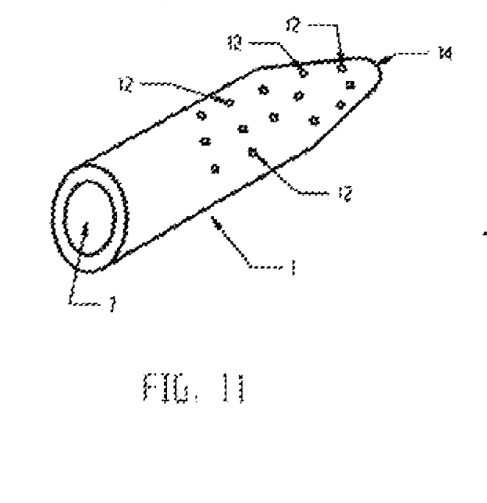
FIG. 11 presents a three-dimensional view of an alternative embodiment of the ultrasonic tip comprising multiple orifices on distal end of the ultrasonic tip.

Chamber 7 may direct cryogenic fluid through one or more orifice 12 in distal end 14 (FIGS. 8, 9, and 10) or one the radial surface of ultrasonic tip 1 (FIG. 11).

Figure 4:
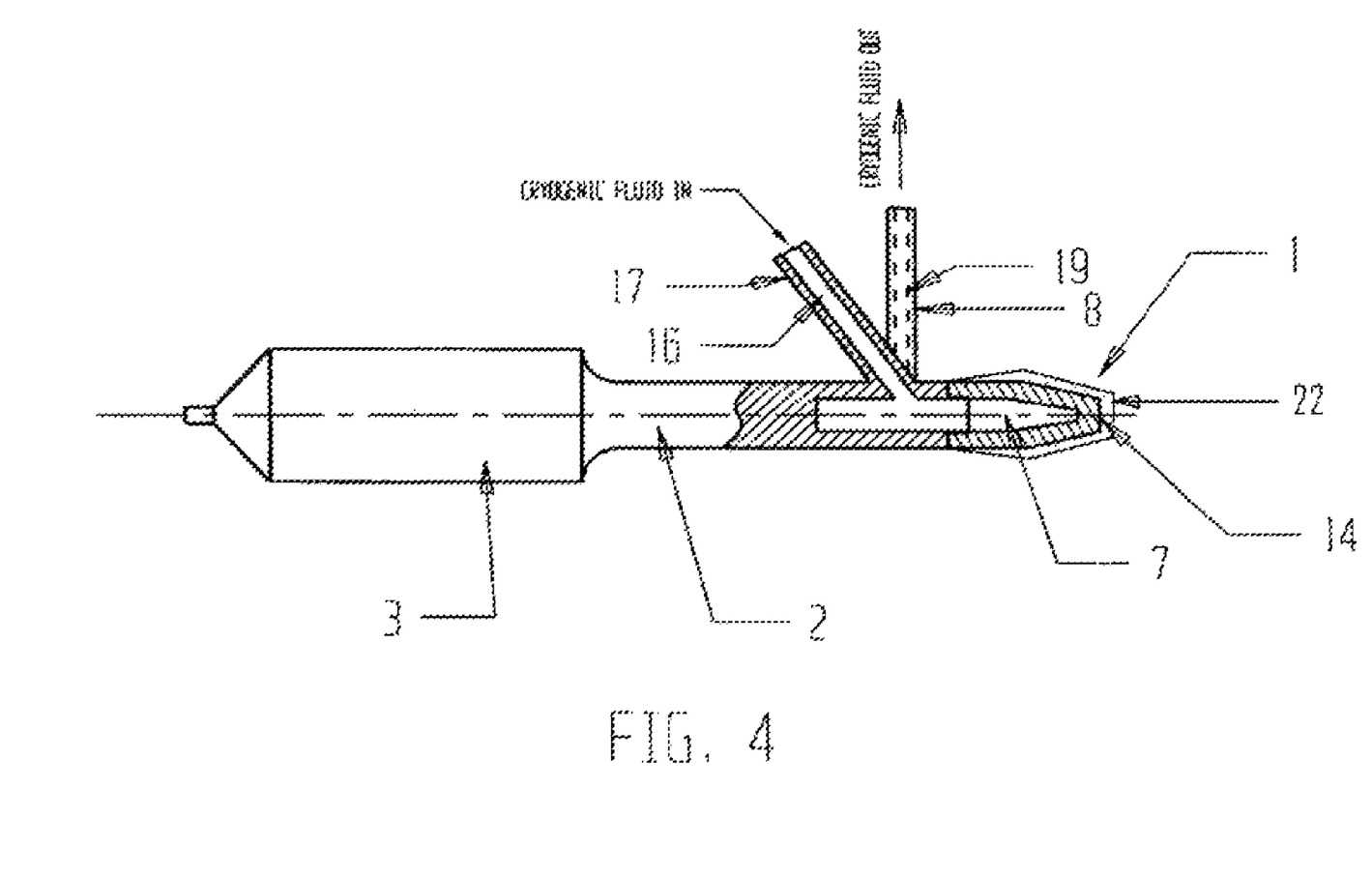
FIG. 4 illustrates an alternative embodiment of an apparatus in accordance with the present invention comprising a cryogenic fluid outlet tube defining an interior passage.

FIG. 4 illustrates an alternative embodiment of an apparatus in accordance with the present invention comprising a cryogenic fluid outlet tube 18 defining an interior passage 19. Permitting the escape of cryogenic fluid from chamber 7, tube 18 enables the circulation of cryogenic fluid through chamber 7.

Figure 5A:
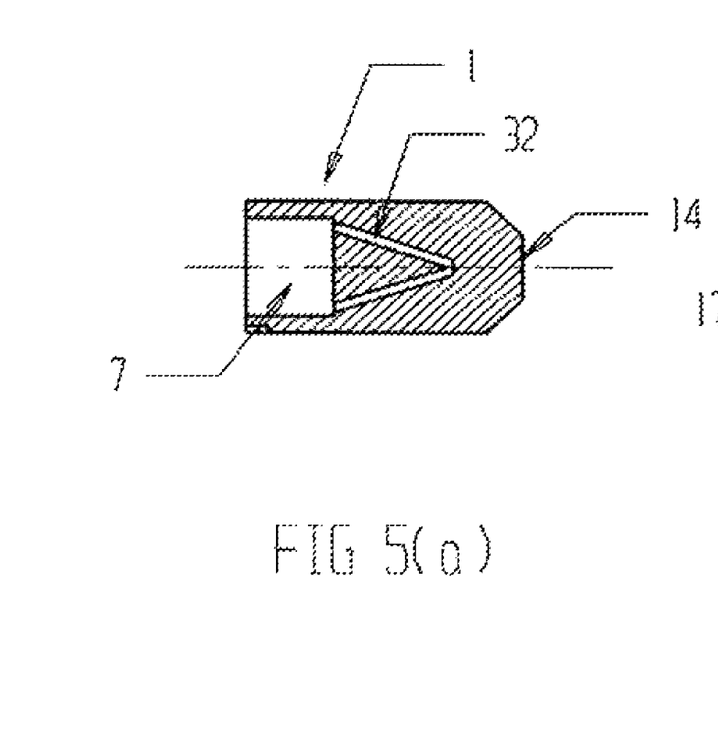
FIG. 5(a) is a side view of a chamber defined by the body of the ultrasonic tip.

FIG. 5(a) is a side view of a chamber 7 defined by body 30 of ultrasonic tip 1. FIG. 5(a) also shows a channel 32 extending through the distal portion of ultrasonic tip 1 and in fluid communication with chamber 7. Such an embodiment may increase the efficacy of heat transfer between ultrasonic tip 1 and the cryogenic fluid 20. A plurality of tubular passages 34 are also defined by the body 30. Emanating from chamber 7 and extending towards distal end 14, tubular passages 34 may allow cryogenic fluid 20 to approach the distal end 14 while the maintaining structural integrity of body 30.

Figure 5B:
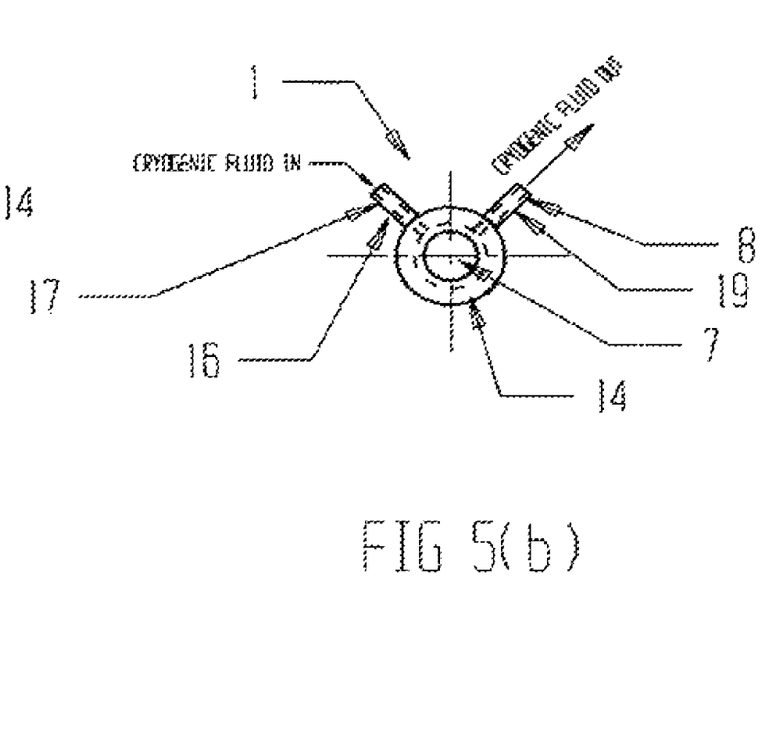
FIG. 5(b) shows a cross-section of an embodiment of the ultrasonic tip with two chambers.

FIG. 5(b) shows a cross-section of an embodiment of ultrasonic tip 1 with two chambers 7. The use of multiple chambers 7 may improve circulation of a cryogenic fluid.

Figure 6:
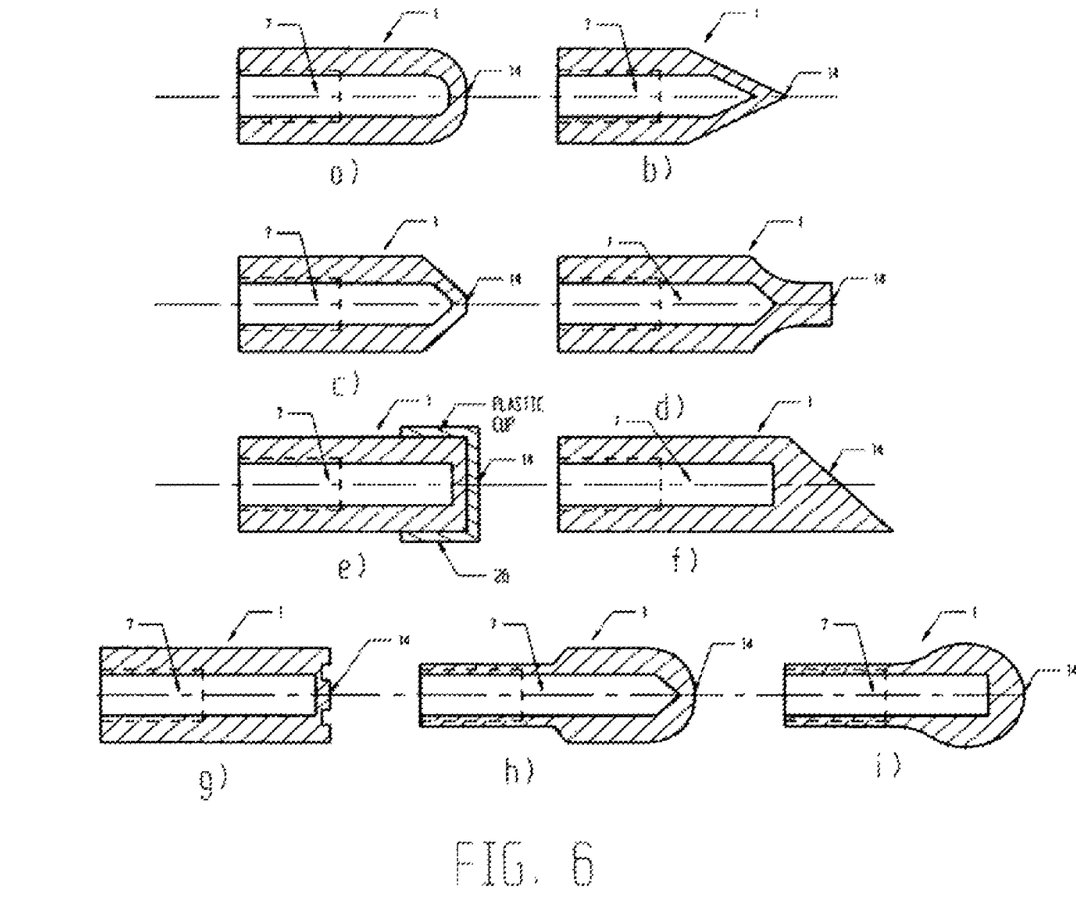
FIG. 6 illustrates cross-sectional views of different possible embodiments of the distal end of the ultrasonic tip.

FIGS. 6(a) to 6(i) are cross-sectional views of different possible embodiments of distal end 14. A rounded or oval distal end, depicted in FIG. 6(a) may be useful for the ablation of large regions of tissue. A sharp cone distal end, depicted in FIG. 6(b), may be useful the precise ablation of small regions of tissue. Flat distal ends, depicted in FIGS. 6(c), 6(d), 6(e), and 6(f), may be useful localized tissue ablation. FIG. 6(g) shows a toothed distal end.

As shown in FIG. 6(e), a disposable plastic cover 26 matching the geometric conformation of distal end 14 may be used to cover distal end 14.

Figure 7:
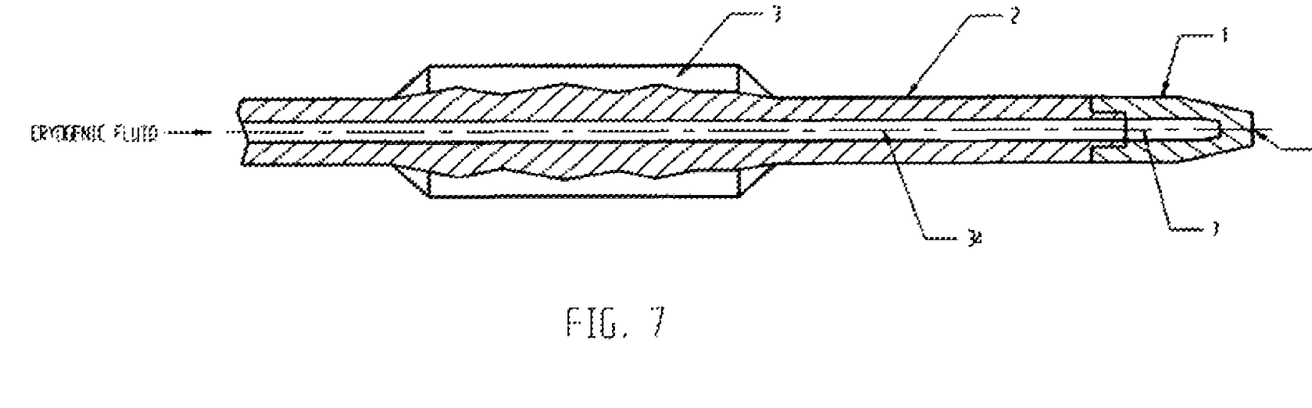
FIG. 7 illustrates the delivery of cryogenic fluid through a lumen passing through the center of the ultrasonic transducer and the horn before connecting to a chamber within the body of the ultrasonic tip.

FIG. 7 illustrates the delivery of cryogenic fluid through a lumen 34 passing through the center of ultrasonic transducer 3 and horn 2 before connecting to chamber 7. This particular embodiment may offer manufacturing advantages readily recognizable to those of ordinary skill in the art.

Figure 8:
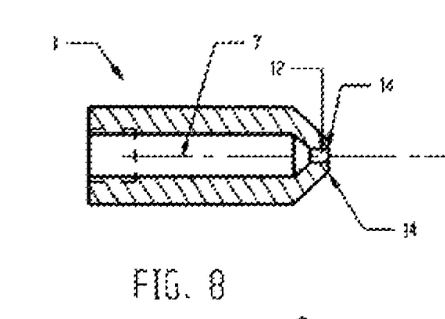
FIG. 8 illustrates an alternative embodiment of the ultrasonic tip comprising an orifice between a chamber within the ultrasonic tip and the distal end of the ultrasonic tip.
Figure 9:
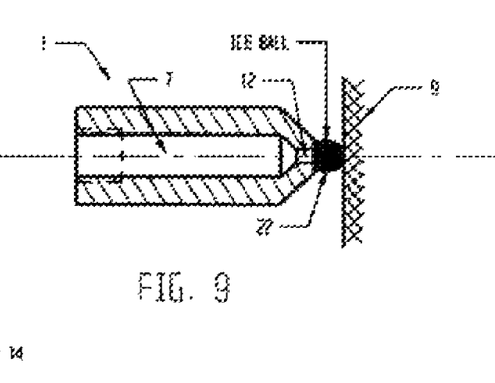
FIG. 9 illustrates an embodiment of the delivery of cryogenic and ultrasonic energy to the tissue through an accumulation of frost positioned between radiation surface and the tissue.

FIG. 8 illustrates an alternative embodiment of ultrasonic tip 1 comprising orifice 12 between chamber 7 and distal end 14. Flowing from chamber 7 through orifice 12, cryogenic fluid 20 emanates from distal end 14, as shown in FIG. 10. Spraying the cryogenic fluid 20 on tissue 9 may allow for the creation of an accumulation of frost 22 on tissue 9. This embodiment may also allow for the creation of an accumulation of frost 22 on distal end 14, as shown in FIG. 9.

FIG. 11 presents a three-dimensional view of an alternative embodiment of ultrasonic tip 1 comprising multiple orifices 12 on distal end 14. This embodiment may be useful for the ablation of tissue forming various lumens in the body such as, but not limited to, bloods vessels.

Figure 12:
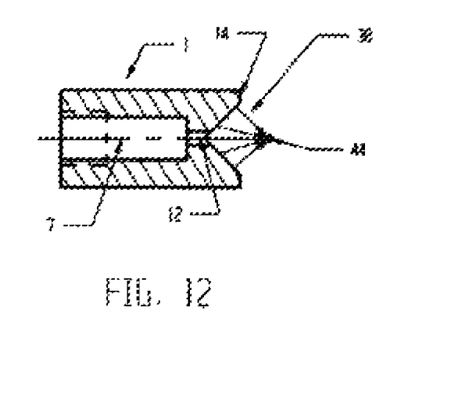
FIG. 12 shows a backwards cone shaped distal end focusing ultrasonic energy on a focal point.

FIG. 12 shows a backwards cone shaped distal end 14 focusing ultrasonic energy on a focal point 44.

Figure 13:
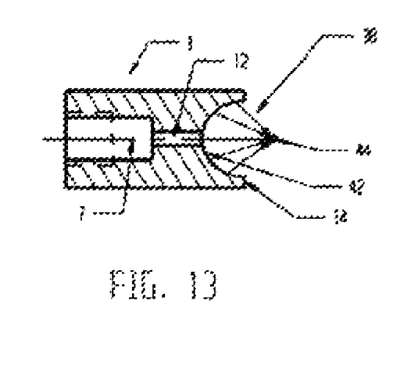
FIG. 13 shows a concave distal end focusing ultrasonic energy on focal point.

FIG. 13 shows a concave distal end 14 focusing ultrasonic energy on focal point 44.

The present invention may be useful for the selective ablation of unwanted and/or diseased tissue. A method in accordance with the present invention comprises the steps of transmitting ultrasonic energy to and transferring thermal energy from a tissue to be ablated. The transfer of thermal energy from the tissue may proceed, follow, and/or occur simultaneously with the transmission of ultrasonic energy to tissue. Transferring thermal energy from the tissue may be accomplished by providing cryogenic fluid 20 to distal end 14 and placing distal end 14 proximate to and/or in contact with the tissue to be ablated. Transmitting ultrasonic energy to the tissue may be accomplished by exciting distal end 14 by activating transducer 3 and placing distal end 14 proximate to and/or in contact with the tissue.

When ultrasonic energy and cryogenic energy are simultaneous delivered to tissue 9 distal end 14 should remain proximate to and/or in contact with the tissue until the unwanted tissue is ablated.

Alternatively, cryogenic energy and the ultrasonic energy may be applied sequentially to the tissue to be ablated. For example, a sequential application may begin by exciting distal end 14, placing the distal end 14 proximate to and/or in contact with the tissue 9, and then providing cryogenic fluid to the distal end 14. The sequence may be reversed, in which case the sequence would begin by providing cryogenic fluid 20 to the distal end 14, allowing an accumulation of frost 22 to form on the distal end 14, placing the distal end 14 proximate to and/or in contact with the tissue 9, and then activating the ultrasonic transducer. Combinations of sequential applications of cryogenic and ultrasonic energy and the simultaneous application of cryogenic and ultrasonic energy may be during ablation of tissue 9 as would be recognized by those skilled in the art.

Alternatively, thermal energy may be transferred away from the tissue by spraying the tissue 9 with a spray of cryogenic fluid 20 emanating from orifice 12 in distal end 14. Exciting distal end 14 as cryogenic fluid 20 sprays from office 12 onto tissue 9 may enable the enable the simultaneous delivery of cryogenic and ultrasonic energy.

If an accumulation of frost 22 is allowed to form on distal end 14 or tissue 9, the accumulation of frost 22 may be used a conduit for the transmission of ultrasonic energy to tissue 9 from distal end 14 and/or the transfer of thermal energy from tissue 9 to distal end 14.

It should be appreciated that as used herein the delivery of cryogenic energy to a tissue is synonymous with transferring cryogenic away from a tissue.

It should be appreciated that as used herein the delivery of ultrasonic energy to a tissue is synonymous with the transmission of ultrasonic energy to a tissue.

It should be appreciated that elements described with singular articles such as "a", "an", and "the" or otherwise described singularly may be used in plurality. It should also be appreciated that elements described in plurality may be used singularly.

Although specific embodiments of apparatuses and methods have been illustrated and described herein, it will be appreciated by people of ordinary skill in the art any arrangement, combination, and/or sequence that is calculated to achieve the same purpose may be substituted for the specific embodiments shown. It is to be understood that above description is intended to be illustrative and not restrictive. Combinations of the above embodiments and other embodiments as wells as combinations and sequences of the above methods and other methods of use will be apparent to individuals possessing skill in the art upon review of the present disclosure. The scope of the present invention should be determined with reference to the appended claims, along with the full scope of equivalents to which such claims are entitled.

I claim:

1. An apparatus comprising:
   a. an ultrasonic tip, comprising:
      i. a body defining a chamber;
      ii. a inlet into the chamber;
      iii. a distal end configured to transfer energy between the body and a tissue; and
      iv. an accumulation of frost on the distal end of the ultrasonic tip;
      v. wherein the inlet delivers a cryogenic fluid into the chamber;
      vi. wherein the chamber is configured to cool the distal end of the body; and
   b. an ultrasonic transducer communicating with the ultrasonic tip to excite the ultrasonic tip.

2. The apparatus of claim 1, wherein the ultrasonic transducer operates at a frequency between approximately 18 KHz and approximately 60 MHz.

3. The apparatus of claim 1, wherein the ultrasonic transducer operates at a frequency between approximately 20 KHz and approximately 100 KHz.

4. The apparatus of claim 1, wherein the ultrasonic transducers operates a frequency of approximately 35 KHz.

5. The apparatus of claim 1, wherein the amplitude of the ultrasonic waves is between approximately 1 micron and approximately 300 microns.

6. The apparatus of claim 1, wherein the amplitude of the ultrasonic wave is approximately 50 microns.

7. The apparatus of claim 1, wherein the distal end is rounded.

8. The apparatus of claim 1, wherein the distal end is rectangular.

9. The apparatus of claim 1, wherein the distal end is pointed.

10. The apparatus of claim 1, wherein the distal end has a sharp edge.

11. The apparatus of claim 1, wherein the distal end has a saw-toothed edge.

12. The apparatus of claim 1, wherein the distal end is concave.

13. The apparatus of claim 1, further comprising one or a plurality of orifices connected to the chamber in the distal end of the ultrasonic tip.

14. The apparatus of claim 1, wherein the distal end is elliptical.

15. A method for removing tissue from a patient, comprising the steps of:
   a. providing an ultrasonic transducer having an ultrasonic tip, comprising:
      i. a body defining a chamber;
      ii. a inlet into the chamber;
      iii. a distal end configured to transfer energy between the body and a tissue; and
      iv. an accumulation of frost on the distal end of the ultrasonic tip;
      v. wherein the inlet delivers a cryogenic fluid into the chamber;
      vi. wherein the chamber is configured to cool the distal end of the body; and
   b. communicating a cryogenic material into the chamber of the ultrasonic tip through the inlet;

c. contacting a tissue of a patient with the distal end of the ultrasonic tip;
d. delivering cryogenic energy from the ultrasonic tip to the tissue through the accumulation of frost on the distal end of the ultrasonic tip;
e. ultrasonically vibrating the ultrasonic tip; and
f. delivering ultrasonic energy from the ultrasonic tip to the tissue through the accumulation of frost on the distal end of the ultrasonic tip.

16. A method for removing tissue from a patient, comprising:
    a. providing an ultrasonic transducer having an ultrasonic tip, comprising:
        i. a body defining a chamber;
        ii. a inlet into the chamber;
        iii. a distal end configured to transfer energy between the body and a tissue; and
        iv. one or a plurality of orifices connected to the chamber in the distal end of the ultrasonic tip;
        v. wherein the inlet delivers a cryogenic fluid into the chamber;
        vi. wherein the chamber is configured to cool the distal end of the body; and
    b. delivering cryogenic energy to the tissue through a cryogenic spray emanating from the distal end of the ultrasonic tip;
    c. allowing an accumulation of frost to form on the tissue
    d. ultrasonically vibrating the ultrasonic tip; and
    e. contacting a tissue of a patient with the distal end of the ultrasonic tip; and
    f. delivering ultrasonic energy from the ultrasonic tip to the tissue through the accumulation of frost on the tissue.

* * * * *